_United States Patent_ [19]

Perrin

[11]  4,360,691

[45]  Nov. 23, 1982

[54] PRODUCTION OF MALONIC ANHYDRIDES AND DERIVATIVES THEREOF

[75] Inventor: Charles L. Perrin, La Jolla, Calif.

[73] Assignee: The Regents of the University of California, Los Angeles, Calif.

[21] Appl. No.: 180,851

[22] Filed: Aug. 25, 1980

Related U.S. Application Data

[62] Division of Ser. No. 904,830, May 11, 1978, Pat. No. 4,251,447.

[51] Int. Cl.$^3$ .................... C07C 67/08; C07C 51/083; C07C 103/14
[52] U.S. Cl. ..................................... 560/131; 560/77; 560/82; 560/204; 562/483; 564/144
[58] Field of Search .................. 560/82, 77, 127, 130, 560/131, 204; 564/134, 144; 562/483

[56] References Cited

U.S. PATENT DOCUMENTS 3,462,535  8/1969  Loev et al. ............................ 560/82
3,758,574  9/1973  Melton et al. ....................... 260/546
4,018,815  4/1977  Vogt et al. ........................... 560/127
4,256,908  3/1981  Nishimura et al. ................. 560/204

FOREIGN PATENT DOCUMENTS 51-108011  9/1976  Japan .................................... 564/144

OTHER PUBLICATIONS

Moriarty et al., Journ. Amer. Chem. Soc., 100:17, pp. 5582-5584.
Cram and Hammond, Organic Chemistry, 2nd Edition, 1964.

_Primary Examiner_—Ethel G. Love
_Attorney, Agent, or Firm_—Albert M. Herzig; Edward C. Walsh; Max Geldin

[57] ABSTRACT

Malonic anhydride and substituted malonic anhydrides are prepared by ozonolysis of the enol-lactone dimers of ketenes. The resulting malonic anhydrides can be hydrolyzed with water to form the corresponding acid, reacted with an alcohol to yield the monoester, or reacted with an amine to yield the monoamide.

10 Claims, No Drawings

PRODUCTION OF MALONIC ANHYDRIDES AND DERIVATIVES THEREOF

This is a division of application Ser. No. 904,830 filed on May 11, 1978 now U.S. Pat. No. 4,251,447.

BACKGROUND OF THE INVENTION

This invention related to the preparation of malonic anhydride and substituted malonic anhydrides, and to the preparation of useful derivatives thereof. The invention is particularly directed to novel procedure for the preparation of malonic anhydrides, particularly malonic anhydride and dimethyl malonic anhydride, and to the preparation of unsymmetrical derivatives of malonic acids, particularly the corresponding monoesters and monoamides, from such anhydrides.

Although the dibasic acids, succinic and glutaric acids, form cyclic anhydrides upon dehydration, dehydration of malonic acid does not yield the anhydride, but leads instead to a gas, carbon suboxide, $C_3O_2$. Although substituted malonic anhydrides can be obtained under dehydrating conditions, these are polymeric and not monomeric.

Further, unsymmetrical derivatives or monoderivatives of malonic acids, such as the monoesters or monoamides, are difficult compounds to prepare and are expensive, such derivatives having utility in the preparation of drugs.

One object of the present invention is the production of malonic anhydride and substituted malonic anhydrides. Another object is the provision of novel procedure for the preparation of malonic anhydride and substituted malonic anhydrides. A further object of the invention is to provide procedure for readily converting malonic anhydrides and substituted malonic anhydrides to derivatives of such anhydrides, particularly the unsymmetrical derivatives such as the monoesters and monoamides. Yet another object is to provide procedure for preparing such derivatives of malonic anhydrides by first preparing the malonic anhydrides and without isolating such anhydrides, reacting the latter in the same solution with a derivatizing agent such as an alcohol or an amine.

SUMMARY OF THE INVENTION

It has now been found according to the invention that malonic anhydride and substituted malonic anhydrides such as dimethylmalonic anhydride, can be prepared by subjecting the appropriate ketene dimer, in the form of an enol-lactone dimer of a ketene, to ozonolysis in an inert solvent, preferably at reduced temperature, and forming a malonic anhydride.

The ozonolysis reaction is carried out by passing ozone through a solution of the ketene dimer starting material in an inert solvent such as methylene chloride, particularly at temperatures generally below 0° C. The anhydrides produced in the reaction are unstable, and decompose at temperatures at or above 0° C., and in some instances below 0° C., e.g. down to −30° C., to $CO_2$ and a ketene.

However, the malonic anhydrides thus produced by ozonolysis can be converted in high yields into the corresponding malonic acids, a monoester or a monoamide, by incorporating a derivatizing agent into the cold solution of the anhydride in the ozonolysis solvent, and then, allowing the mixture to warm to room temperature to complete the reaction in the presence of the derivatizing agent. The resulting derivatives of the malonic anhydrides, such as the corresponding malonic acids, monoesters and monoamides are stable, and need not be used immediately.

Thus, although malonic anhydride and the substituted malonic anhydrides, such as dimethylmalonic anhydride, which are formed in the ozonolysis reaction, can be isolated at low temperatures, it is preferred to react such malonic anhydride in situ in the ozonizing solvent, to produce the desired derivatives. It is feasible according to the invention process also to generate the malonic anhydrides by ozonolysis, and to convert the resulting malonic anhydrides to their derivatives simultaneously, e.g. by carrying out the ozonolysis in a suitable solvent and in the presence of a derivatizing agent such as an alcohol.

DESCRIPTION OF PREFERRED EMBODIMENTS

The reaction for ozonizing an enol-lactone dimer of ketene, such as diketene, to produce malonic anhydride or substituted malonic anhydrides is represented by equation (1) below.

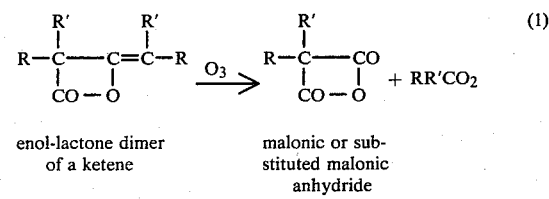

enol-lactone dimer of a ketene → malonic or substituted malonic anhydride where R and R' can be hydrogen, alkyl, generally having a chain length ranging from $C_1$ to $C_{20}$, cycloalkyl, e.g. containing from about 3 to about 8 carbon atoms, heterocyclic, e.g. five and six membered heterocyclic rings containing oxygen or nitrogen, aryl (including unsubstituted aryl and alkylated aryl, e.g. aralkyl and alkaryl), such aryl groups containing from about 6 to about 20 carbon atoms, and where R and R' can be the same or different, or R and R' together can constitute the atoms necessary to form a carbocyclic ring, e.g. of from about 4 to about 8 carbon atoms. Examples of such groups include methyl, ethyl, n-propyl, isopropyl, n-butyl, isobutyl, n-pentyl cyclopentyl, cyclohexyl, pyridyl, tetrahydropyranyl, tetrahydrofuryl, phenylmethyl, phenyl, methyl, phenylethyl, tolyl, xylyl, and the like, or where R and R' together can constitute the atoms necessary to complete a tetramethylene or pentamethylene group, and the like. The R and R' groups can also carry substituents such as halogen, nitro, ether, ester, ketone and aldehyde groups, and also amine, olefinic, acetylenic, and heterocyclic groups that are less reactive toward ozone than the enol lactone. Also such R and R' groups can carry any substituents, such as hydroxyl, carboxyl, and amino, whose reaction with the anhydride could be expected not to interfere with subsequent conversion reactions of the malonic anhydrides.

The ozonolysis reaction is carried out in a suitable inert solvent. Suitable solvents for this purpose have been found to be dry $CH_2Cl_2$, $CS_2$ and ethyl acetate. Other suitable inert organic solvents for ozonolysis include $CCl_4$, acetone, chloroform, ether, tetrahydrofurane (THF), dioxane, pyridine, and a saturated hydrocarbon such as pentane or hexane. Also solvents can be employed which can react with the malonic anhydride formed in the reaction and convert it to a derivative thereof substantially concurrently with the ozonolysis, such as an alcohol, e.g. methanol, ethanol, and the like, or liquid ammonia, or an amine, as described in greater detail below. Mixtures of the above solvents can also be employed.

Ozone generated by an ozonator is passed through the solution of the enol-lactone dimer to carry out the ozonolysis reaction. An amount of ozone is employed to convert substantially all of the enol-lactone dimer of the ketene to the corresponding malonic anhydride in high yield approaching 100% based on the diketene starting material. In examples of ozonolysis carried out according to the invention, ozone was generated in an Orec model 03V5-0 Ozonator, producing about 0.4% ozone in oxygen, at a flow rate of 1.5 liters/min. Completion of the reaction was indicated by the blue color of excess ozone in the reaction mixture.

Since the anhydrides produced are unstable at room temperature, ozonolysis is generally carried out at temperatures below about 0° C., ranging from about −100° C. to about 0° C. Preferably the ozonolysis reaction is carried out at between about −100° C. and −50° C. However, it is possible to carry out the ozonolysis at temperatures above 0° C. and up to ambient temperature (20°-25° C.) in the presence of nucleophiles or derivatizing agents such as amines, alcohols and water, with a basic catalyst added, if desired, to trap the anhydride formed in the ozonolysis reaction and immediately convert it to a derivative of the anhydride faster than it decomposes. As previously noted, under these conditions such derivatizing agents may function as solvents for the ozonolysis also.

Since as previously noted, the anhydrides formed during ozonolysis are unstable and generally decompose at or below 0° C., usually no attempt is made to isolate and recover the malonic anhydrides formed during ozonolysis, but rather the anhydride formed is converted directly to a desired derivative thereof by adding an excess of derivatizing agent to the cold solution of the anhydride in the ozonolysis solvent. Such derivatizing agent can be a hydrolyzing agent such as water, which converts the malonic anhydride to the corresponding malonic acid, a hydroxyl containing organic compound such as an alcohol or a phenol for conversion of the malonic anhydride to a monoester, or ammonia or an amine such as an aliphatic or an aromatic amine to convert the anhydride to the corresponding monoamide. Following addition of the derivatizing agent to the cold solution of the anhydride, the mixture is allowed to warm to room temperature to complete the derivatization reaction. The amount of derivatizing agent employed is at least one mol per mol of the malonic anhydride in order to obtain the unsymmetrical monoester or monoamide. Usually an excess greater than stoichiometric proportions of derivatizing agent to the malonic anhydride is employed. Generally, high yields of the malonic acid derivatives are obtained in the reaction, ranging from 70% to close to 100%, based on the ketene dimer starting material.

The reaction for converting the malonic anhydride to the corresponding malonic acid, a monoester or a monoamide is illustrated by equation (2) below:

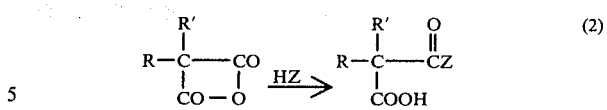

where R and R' have the values noted above, and Z can be OR" or NR$_2$", where R" is hydrogen, alkyl, generally of about 1 to about 18 carbon atoms, such as methyl, ethyl, n-propyl, isopropyl, and the like, aryl (including unsubstituted aryl and alkylated aryl groups), such aryl groups containing from about 6 to about 14 carbon atoms, such as phenyl, phenyl methyl, phenyl ethyl, and the like. The R" groups in NR$_2$" can be the same or different.

Conversion of the malonic anhydrides to the corresponding monoester or monoamide is a very facile reaction, due to the characteristics of the four-membered malonic anhydride ring. To convert the monoester or monoamide to the diester, diamide or ester-amide, more vigrous reaction conditions are required, such as treatment of the monoester or monoamide with thionyl chloride (SOCl$_2$), followed by reaction of the resultant ester-chloride or amide-chloride with alcohol or amine.

As previously noted, malonic anhydrides are unstable and decompose to CO$_2$ and a ketene. Malonic anhydride itself undergoes partial decomposition within one hour at −30° C. Dimethylmalonic anhydride is more stable but appears to undergo decomposition near +10° C. Decomposition is even faster at higher temperatures.

However, the malonic anhydrides formed in the ozonolysis reaction can be isolated at low temperture, as by proper choice of solvent, to permit separation thereof from the ketone or aldehyde peroxide formed in the reaction. Thus, malonic anhydride can be crystallized from the reaction mixture following ozonolysis in CS$_2$ in which the anhydride is only slightly soluble at −78° C. However, it is preferred to convert the malonic anhydrides directly to their derivatives in the ozonolysis solution, by allowing such solution to warm to room temperature in the presence of the derivatizing agent.

Further, if desired, the ozonolysis reaction for generating the malonic anhydride and the subsequent reaction for converting the malonic anhydride to its derivative can be carried out simultaneously. As previously indicated, this can be done by carrying out the ozonolysis reaction in the presence of an alcohol or an amine, to convert the malonic anhydride formed in the ozonolysis reaction immediately to the monoester or monoamide derivative. Thus, reactions (1) and (2) above can be carried out simultaneously in the same solvent solution.

There are no major by-products formed in reactions (1) and (2) above, other than the ketone peroxide or aldehyde peroxide formed during the ozonolysis reaction (1), and the final malonic acid derivatives formed in the derivatizing reaction are readily separated from these by-products by extracting the malonic acid derivatives with a suitable solvent such as ether or alkali.

The following are examples of practice of the invention.

EXAMPLE I

A steady stream of ozone was passed into a solution of redistilled diketene (100 μl) in dry CH$_2$Cl$_2$ (3 ml) in a flask equipped with an outlet leading to an ozone trap. The reaction mixture was maintained near −78° C. in a Dry Ice-isopropanol bath. After ozonolysis was completed, the mixture was flushed with dry nitrogen to expel excess ozone. The solution contained malonic anhydride and formaldehyde peroxide (in the form of its oligomers).

To the cold solution of malonic anhydride, prepared as above, was added aniline (700 μl, 6 equivalents). The reaction mixture was allowed to warm to room temperature. It was then extracted with 5 ml saturated aqueous $NaHCO_3$, and the aqueous extract was washed with 5 ml ether, acidified with $H_2SO_4$, and extracted with 3-4-ml portions of ether. The ether extracts were combined and dried over $Na_2SO_4$, and the ether was removed under reduced pressure, to leave a residue of malonanilide (mp 127°–130° C., 180 mg, 72% isolated yield, based on diketone).

EXAMPLE II

A solution of 3-hydroxy-2,2,4-trimethyl-3-pentenoic acid β-lactone (100 μl) in dry $CH_2Cl_2$ (3 ml) was ozonized in the same manner as was diketene (above). The resulting solution contained dimethylmalonic anhydride and oligomeric acetone peroxide.

To a cold solution of dimethylmalonic anhydride, prepared as above, was added absolute ethanol (1 ml, 25 equivalents). The reaction mixture was allowed to warm to room temperature, and then treated as in preparation of malonanilide, to produce monoethyl dimethylmalonate (130 mg, 76% isolated yield, based on the enol lactone).

EXAMPLE III

Diketene was ozonized substantially as described in Example I above, and was reacted with ethanol, and phenol, respectively, as described essentially in Example II above, to form the monoethyl ester of malonic acid in an isolated yield of 76%, and the monophenyl ester of malonic acid in an isolated yield of 56%, respectively, based on diketene.

EXAMPLE IV

Dimethylmalonic anhydride was prepared by ozonolysis in the manner described in Example II above, and the resulting reaction mixture was then reacted with aniline essentially as described in Example I above, to form the monoanilide of dimethylmalonic acid in an isolated yield of 84% based on enol-lacetone.

From the foregoing, it is seen that the invention provides procedure for the production of malonic anhydrides which avoids the dehydration methods usually employed for producing anhydrides, and utilizing an already formed four-membered ring, by ozonolysis of the enol-lactone dimers of ketenes. The ozonolysis is carried out preferably at reduced temperature to avoid decomposition of the malonic anhydride formed in the reaction, and the malonic anhydrides formed are readily converted to malonic acid or substituted malonic acids, or to useful derivatives of malonic and substituted malonic acids, such as the monoesters and monoamides of such malonic acids, simply by adding the derivatizing agent to the ozonolysis reaction mixture following formation of the malonic anhydride and permitting the temperature thereof to rise, or by carrying out the ozonolysis reaction in the presence of the derivatizing agent to convert the malonic acid formed, directly to the desired derivatives of the malonic acids. The latter reaction can be carried out at temperatures up to ambient.

The malonic acid derivatives produced according to the invention can be used in synthesizing organic chemicals and particularly in the pharmaceutical field for the production of drugs such as phenobarbital, barbital, primaclone, meprobamate, and analogs thereof.

While particular embodiments of the invention have been described for the purpose of illustration within the spirit of the invention, it will be understood that the invention is not to be taken as limited except by the scope of the appended claims.

What is claimed is:

1. A process for producing a derivative of a malonic anhydride selected from the group consisting of a malonic acid, a malonic acid monoester and a malonic acid monoamide, which comprises passing ozone through an inert organic solvent containing an enol-lactone dimer of a ketene, said dimer of a ketene having the general formula

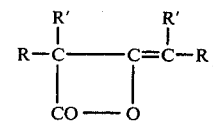

where R and R' are selected from the group consisting of hydrogen, alkyl having a chain length ranging from $C_1$ to $C_{20}$, cycloalkyl containing from about 3 to about 8 carbon atoms, carbocyclic aryl, said aryl groups containing from about 6 to about 20 carbon atoms, and where R and R' can be the same or different, and where R and R' together can constitute the atoms necessary to form a carbocyclic ring of from about 4 to about 8 carbon atoms, said solvent being maintained at a temperature ranging from about −100° C. to about 0° C., and forming a malonic anhydride having the formula

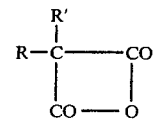

where R and R' are defined as above, adding a derivatizing agent selected from the group consisting of water, alcohols, phenols, ammonia and amines to the reaction mixture, and permitting the reaction mixture to warm to about room temperature.

2. The process as defined in claim 1, wherein said derivative is a compound having the general formula

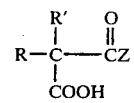

where R and R' are selected from the group consisting of hydrogen, alkyl having a chain length ranging from $C_1$ to $C_{20}$, cycloalkyl containing from about 3 to about 8 carbon atoms, carbocyclic aryl, said aryl groups containing from about 6 to about 20 carbon atoms, and wherein R and R' can be the same or different, and where R and R' together can constitute the atoms necessary to form a carbocyclic ring of from about 4 to about 8 carbon atoms, and Z is selected from the group consisting of OR'' and $NR_2''$, where R'' is selected from the group consisting of hydrogen, alkyl of from about 1 to about 18 carbon atoms and aryl of from about 6 to about 14 carbon atoms.

3. The process as defined in claim 1, wherein said ketene dimer is diketene, and the malonic anhydride formed is malonic anhydride.

4. The process as defined in claim 3, wherein sufficient of said derivatizing agent is employed to produce a high yield of malonic acid, a monoester of malonic acid, or a monoamide of malonic acid, based on said ketene dimer.

5. The process as defined in claim 1, wherein said ketene dimer is 3-hydroxy-2,2,4-trimethyl-3-pentenoic acid β-lactone, and wherein said malonic anhydride is dimethyl malonic anhydride.

6. The process as defined in claim 5, wherein sufficient of said derivatizing agent is employed to produce a high yield of dimethylmalonic acid, a monoester of dimethyl malonic acid, or a monoamide of dimethyl malonic acid, based on said ketene dimer.

7. The process as defined in claim 1, said derivatizing agent being present during ozonolysis and also being the solvent for said ozonolysis.

8. The process as defined in claim 1, said ketene dimer selected from the group consisting of diketene and 3-hydroxy-2,2,4-trimethyl-3-pentenoic acid β lactone, and said malonic anhydride selected from the group consisting of malonic anhydride and dimethylmalonic anhydride, said reaction with derivatizing agent taking place substantially concurrently with said ozonolysis.

9. A process for producing a derivative of a malonic anhydride selected from the group consisting of a malonic acid monoester and a malonic acid monoamide, which comprises subjecting an enol-lactone dimer of a ketene to ozonolysis in an inert solvent, and forming a malonic anhydride, said enol-lactone dimer of a ketene having the general formula:

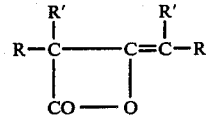

where R and R' are selected from the group consisting of hydrogen, alkyl, cycloalkyl, carbocyclic aryl, and where R and R' can be the same or different, and where R and R' together can constitute the atoms necessary to form a carbocyclic ring, adding a derivatizing agent to the solution, said derivatizing agent being selected from the group consisting of alcohols, phenols, ammonia and amines, and forming the corresponding malonic acid monoester or malonic acid monoamide derivative of said malonic anhydride.

10. The process as defined in claim 9, wherein said solvent during ozonolysis is maintained at a temperature below about 0° C., and said derivatizing agent is added to the reaction mixture following ozonolysis, and thereafter permitting the temperature of the reaction mixture to rise, and forming said malonic anhydride derivative.

* * * * *